US00PP12270P2

(12) United States Plant Patent
Tucker

(10) Patent No.: US PP12,270 P2
(45) Date of Patent: Dec. 11, 2001

(54) MINIATURE ROSE PLANT NAMED 'TUCKAMY'

(76) Inventor: Robert T. Tucker, 9404 Hunting Hills Dr., Franklin, TN (US) 37607

( * ) Notice: Subject to any disclaimer, the term of this patent is extended or adjusted under 35 U.S.C. 154(b) by 0 days.

(21) Appl. No.: 09/476,812

(22) Filed: Jan. 3, 2000

(51) Int. Cl.[7] ..... A01H 5/00

(52) U.S. Cl. ..... Plt./128; Plt./121

(58) Field of Search ..... Plt./128, 123, 121, Plt./116, 118, 124

*Primary Examiner*—Howard J. Locker

(57) ABSTRACT

This invention relates to a new and distinct variety of miniature rose plant primarily identified by its light pink buds and flowers, hybrid tea form and glossy dark green foliage.

1 Drawing Sheet

The present invention relates to a new and distinct variety of hardy, dwarf, bush type rose plant of the miniature class; the variety being primarily characterized—as to novelty—by buds and flowers of a light pink color which generally are of exhibition (hybrid tea) form.

The variety is further characterized by:

An abundance of bloom, with flowers often borne singly and also several to the stem in loose clusters.

Medium fragrance.

A plant which is vigorous, upright shape with medium growth habit and dark green glossy foliage.

A plant which has an average height by 14–24 inches, can easily be maintained at lesser height by occasional trimming.

A plant which grows and blooms satisfactorily both in the greenhouse and outdoors; is good for growing in pots; and provides excellent garden decoration as well as cut flowers.

The present variety of miniature rose was originated by me in my hybridizing garden located at Franklin, Tenn. under conditions of careful control and observation, as a cross between miniature rose Loving Touch (not patented) as the seed parent and the hybrid tea, White Masterpiece (U.S. Plant Pat. No. 2,998) as the pollen parent.

Subsequent to origination of the variety, I successfully asexually reproduced it at my hybridizing garden, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The Royal Horticultural Society Colour Chart, except where common terms of color definition are employed.

Class: Miniature. Variety identification : TUCkamy (Commercial synonym: Amy Grant).

FLOWER

Observations made from specimens grown in a garden environment at Franklin, Tenn. in May 1995 through September 1999.

Blooming habit: Continuous.

Bud:

*Size.*—½ to ¾ inch long when the petals start to unfurl.

*Form.*—The bud form is a pointed oval shape and of medium length.

*Color.*—When the sepals first divide, bud color is Red Purple Group 68D.

*Sepals.*—Color: Medium green. Surface texture: Smooth.

*Peduncle.*—Length: Medium to long. 1 to 2.5 inches. Surface: Mostly smooth. Some very fine hairs. Strength: Stiff. Color: Light green.

Bloom:

*Size.*—Medium to Large for a dwarf-type rose; Average open size is 2 to 3 inches across.

*Borne.*—Singly and sometimes in clusters of 2 to 4 flowers.

*Stems.*—Long and strong.

*Form.*—High centered; exhibition; Reflexed petals; When fully open stamens show.

*Petalage.*—Double; Number of petals under normal conditions: 17–25. Arranged regularly plus some small petaloids. Petals have medium substance.

*Color.*—The Bud color is Red Purple Group 68D. The petals' upper and lower sides at ¾ open stage to fully open appear to the eye as very light pink. Actual color is White Group 155C. There can be some slight hints of yellow near the petals' base in cool weather with petals color Red Purple Group 68D in center petals and outer petals changing to White Group 155B. The petals tend to be almost white in hot weather.

*Variegations.*—None.

*Discoloration.*—The general tonality at the end of the first day: No change. At the end of the third day: Some fading. At the end of the bloom cycle fades almost white.

*Fragrance.*—Medium Fragrance.

Reproductive parts:

*Anthers.*—Size: Medium; Quantity: Many; Color: Medium Yellow; Arrangement: Regular around styles.

*Filaments.*—Varying length, mostly short, yellowish.

*Pollen.*—Quantity: Very heavy; Color: Golden yellow.

*Styles.*—Color: reddish.

*Stigmas.*—Color: light yellow.
*Ovaries.*—All enclosed in calyx.
*Hips.*—Sets Hips readily.
*Seeds.*—Medium to Large for Dwarf plant.

Growth:
*Habit.*—Dwarf; mostly upright; vigorous to 24 inches.

Foliage:
*Leaflets.*—Number on normal mid-stem leaves: 5 or 7.
*Size.*—Small to Medium; Leaflets vary in length from ½ to 1½ inches.
*Quantity.*—Abundant.
*Color.*—New foliage: Upper side Green Group 139A; Under side Green Group 137D.
*Old foliage.*—Upper surface: Green Group 133A; Lower surface: Green Group 139C.

Leaflets:
*Shape.*—Pointed oval.
*Texture.*—Smooth; Glossy.
*Edge.*—Serrated.
*Serration.*—Single, small.
*Petiole rachis.*—Smooth and light green.
*Petiole underside.*—Smooth.
*Stipules.*—Medium to short length (¼ to ½ inch).

Wood:
*New wood.*—Color: Reddish but turns light green very quickly. Bark smooth.
*Old wood.*—Color: medium green; Bark smooth.

Prickles:
*Quantity.*—Average.
*Form.*—Varying sizes from small prickles to medium thorns; Medium thorn size (⅜ inch); Prickles straight and point down (approximately 45 degrees) from stem.

The miniature rose plant and its flowers as herein described may vary in slight detail due to climatic, soil and cultural conditions under which the variety may be grown; the present description being of the variety as grown at Franklin, Tenn.

The following is claimed:

1. A new and distinct variety of miniature rose plant of hardy, dwarf, upright habit, substantially as illustrated and described, characterized by buds and flowers of exhibition (hybrid tea) form, essentially light pink in color, with reverse the same, and further characterized by a plant of upright shape, vigorous, with the main stems and shoots being moderately thorny, the said plant being easy to propagate from cuttings, with an abundance of flowers borne singly or several to a stem.

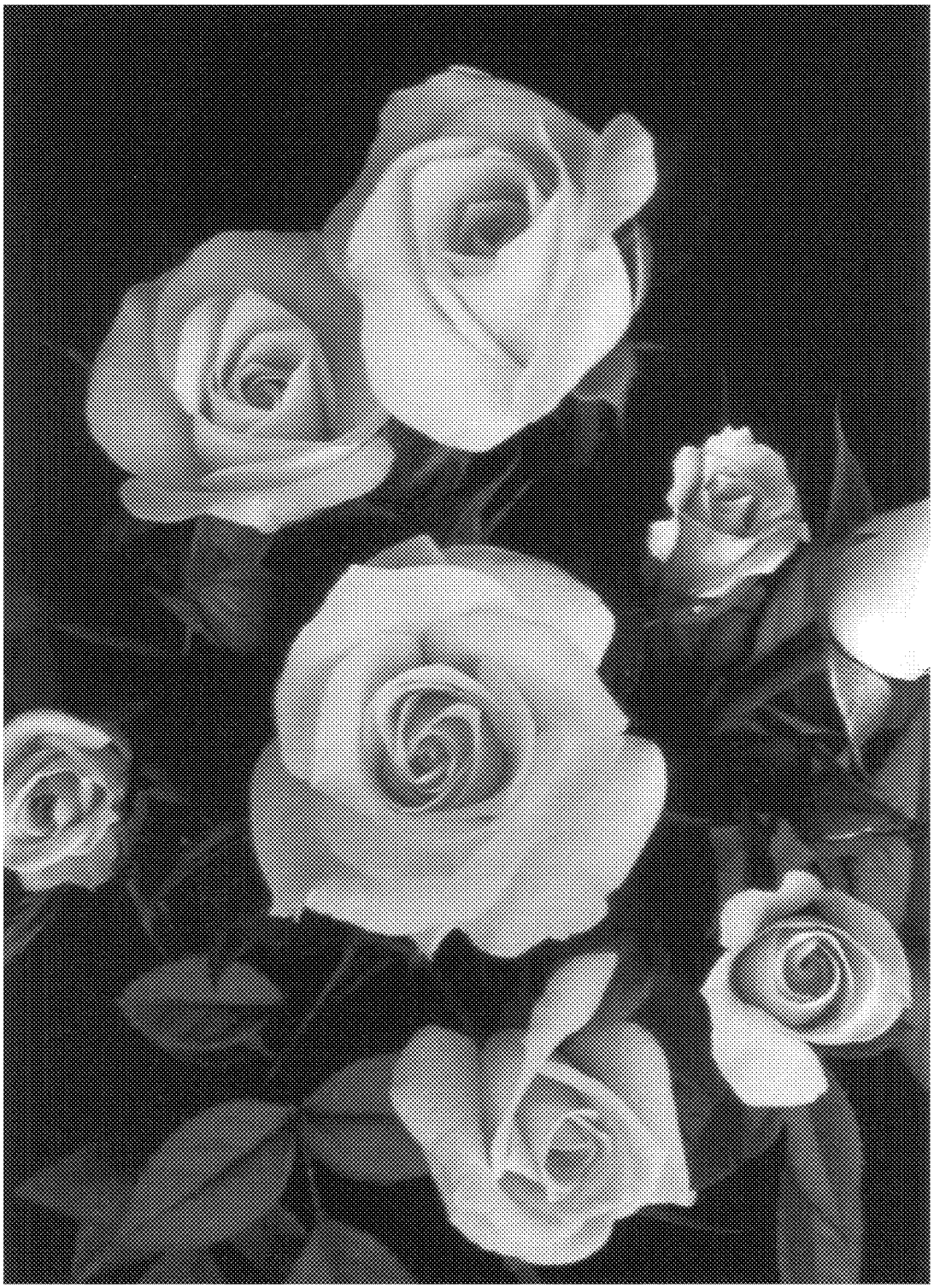

* * * * *